US010234767B2

(12) United States Patent
Goorden et al.

(10) Patent No.: US 10,234,767 B2
(45) Date of Patent: Mar. 19, 2019

(54) DEVICE AND METHOD FOR PROCESSING A RADIATION BEAM WITH COHERENCE

(71) Applicant: ASML Netherlands B.V., Veldhoven (NL)

(72) Inventors: Sebastianus Adrianus Goorden, Eindhoven (NL); Nitesh Pandey, Eindhoven (NL); Duygu Akbulut, Eindhoven (NL); Teunis Willem Tukker, Eindhoven (NL); Johannes Matheus Marie De Wit, Helmond (NL)

(73) Assignee: ASML Netherlands B.V., Veldhoven (NL)

( * ) Notice: Subject to any disclaimer, the term of this patent is extended or adjusted under 35 U.S.C. 154(b) by 0 days.

(21) Appl. No.: 15/660,498

(22) Filed: Jul. 26, 2017

(65) Prior Publication Data

US 2018/0031977 A1 Feb. 1, 2018

(30) Foreign Application Priority Data

Aug. 1, 2016 (EP) .................................... 16182256

(51) Int. Cl.
*G03F 7/20* (2006.01)
*G01N 21/88* (2006.01)
(Continued)

(52) U.S. Cl.
CPC ....... *G03F 7/7015* (2013.01); *G01N 21/8806* (2013.01); *G01N 21/9501* (2013.01);
(Continued)

(58) Field of Classification Search
CPC .......... G01N 21/8806; G01N 21/9501; G01N 2021/0631; G01N 2021/8822;
(Continued)

(56) References Cited

U.S. PATENT DOCUMENTS

| 4,011,403 A | 3/1977 | Epstein et al. |
| 5,898,802 A | 4/1999 | Chen et al. |

(Continued)

FOREIGN PATENT DOCUMENTS

| KR | 10 2007 0029231 A | 3/2007 |
| WO | WO 2009/078708 A1 | 6/2009 |

(Continued)

OTHER PUBLICATIONS

"A Chaotic Approach to Speckle-Free Lasing," Optics and Photonics News, The Optical Society, Dec. 2015; 4 pages.
(Continued)

*Primary Examiner* — Colin Kreutzer
(74) *Attorney, Agent, or Firm* — Sterne, Kessler, Goldstein & Fox P.L.L.C.

(57) ABSTRACT

Devices and methods for processing a radiation beam with coherence are disclosed. In one arrangement, an optical system receives a radiation beam with coherence. The radiation beam comprises components distributed over one or more radiation beam spatial modes. A waveguide supports a plurality of waveguide spatial modes. The optical system directs a plurality of the components of the radiation beam belonging to a common radiation beam spatial mode and having different frequencies onto the waveguide in such a way that each of the plurality of components couples to a different set of the waveguide spatial modes, each set comprising one or more of the waveguide spatial modes.

19 Claims, 6 Drawing Sheets

(51) Int. Cl.
*G01N 21/95* (2006.01)
*G02B 6/26* (2006.01)
*G02B 6/42* (2006.01)

(52) U.S. Cl.
CPC ......... *G02B 6/262* (2013.01); *G03F 7/70075* (2013.01); *G03F 7/70583* (2013.01); *G03F 7/70616* (2013.01); *G03F 7/70625* (2013.01); *G03F 7/70633* (2013.01); *G01N 2021/8822* (2013.01); *G01N 2201/0631* (2013.01); *G02B 6/4204* (2013.01); *G02B 6/4296* (2013.01)

(58) Field of Classification Search
CPC .... G02B 6/262; G02B 6/4204; G02B 6/4269; G03F 7/70075; G03F 7/7015; G03F 7/70583; G03F 7/70616; G03F 7/70625; G03F 7/70633
USPC ....................... 355/67, 71; 362/551, 558, 575
See application file for complete search history.

(56) References Cited

U.S. PATENT DOCUMENTS

| | | |
|---|---|---|
| 7,697,128 B2 | 4/2010 | Snel et al. |
| 7,834,980 B2 | 11/2010 | Baselmans et al. |
| 8,921,814 B2 | 12/2014 | Pellemans et al. |
| 8,937,706 B2 | 1/2015 | Mulder et al. |
| 9,304,077 B2 | 4/2016 | Stevens et al. |
| 2002/0030807 A1 | 3/2002 | Maeda et al. |
| 2006/0066855 A1 | 3/2006 | Boef et al. |
| 2009/0110013 A1 | 4/2009 | Gollier et al. |
| 2011/0027704 A1 | 2/2011 | Cramer et al. |

FOREIGN PATENT DOCUMENTS

| | | | |
|---|---|---|---|
| WO | WO 2009/106279 A1 | 9/2009 | |
| WO | WO 2012/164539 A1 | 12/2012 | |
| WO | WO 2014/187656 A1 | 11/2014 | |
| WO | WO 2017027862 A1 * | 2/2017 | ......... H01S 3/06729 |

OTHER PUBLICATIONS

International Search Report and Written Opinion of the International Searching Authority directed to related International Patent Application No. PCT/EP2017/068047, dated Oct. 18, 2017; 14 pages.

* cited by examiner

DEVICE AND METHOD FOR PROCESSING A RADIATION BEAM WITH COHERENCE

FIELD

The present invention relates to a device and method for processing a radiation beam with coherence, to an inspection apparatus and inspection method, and to a lithographic apparatus and method of performing a lithographic process.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., comprising part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

In order to monitor the lithographic process, parameters of the patterned substrate are measured. Parameters may include, for example, the overlay error between successive layers formed in or on the patterned substrate and critical dimension (typically linewidth) of developed photosensitive resist and/or etched product features. This measurement may be performed on a product substrate and/or on a dedicated metrology target. There are various techniques for making measurements of the microscopic structures formed in lithographic processes, including the use of scanning electron microscopes and various specialized tools. A fast and non-invasive form of specialized inspection tool is a scatterometer in which a beam of radiation is directed onto a target on the surface of the substrate and properties of the scattered or reflected beam are measured. By comparing the properties of the beam before and after it has been reflected or scattered by the substrate, the properties of the substrate can be determined. This can be done, for example, by comparing the reflected beam with data stored in a library of known measurements associated with known substrate properties. Two main types of scatterometer are known. Spectroscopic scatterometers direct a broadband radiation beam onto the substrate and measure the spectrum (intensity as a function of wavelength) of the radiation scattered into a particular narrow angular range. Angularly resolved scatterometers use a monochromatic radiation beam and measure the intensity of the scattered radiation as a function of angle.

Lasers have been used to provide the beam of radiation for inspection of the metrology targets. Lasers are capable of providing beams with high intensity. It has proven difficult, however, to provide a low cost system that is able to provide an intensity that is spatially uniform (e.g. without speckle or fringes) and stable over time.

SUMMARY

It is desirable to provide a high intensity radiation beam which is spatially uniform and stable over time, particularly for the purpose of inspecting a metrology target as part of a lithographic process.

According to an aspect of the invention, there is provided a device for processing a radiation beam with coherence, comprising: an optical system configured to receive a radiation beam with coherence, the radiation beam comprising components distributed over one or more radiation beam spatial modes; and a waveguide configured to support a plurality of waveguide spatial modes, wherein: the optical system is configured to direct a plurality of the components of the radiation beam belonging to a common radiation beam spatial mode and having different frequencies onto the waveguide in such a way that each of the plurality of components couples to a different set of the waveguide spatial modes, each set comprising one or more of the waveguide spatial modes.

According to an aspect of the invention, there is provided a method of processing a radiation beam with coherence, comprising: receiving a radiation beam with coherence, the radiation beam comprising components distributed over one or more radiation beam spatial modes; passing the radiation beam through an optical system which directs the components onto a waveguide supporting a plurality of waveguide spatial modes, wherein: the optical system directs a plurality of the components of the radiation beam belonging to a common radiation beam spatial mode and having different frequencies onto the waveguide in such a way that each of the plurality of components couples to a different set of the waveguide spatial modes, each set comprising one or more of the waveguide spatial modes.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION OF EXEMPLARY EMBODIMENTS

This specification discloses one or more embodiments that incorporate the features of this invention. The disclosed embodiment(s) merely exemplify the invention. The scope of the invention is not limited to the disclosed embodiment(s). The invention is defined by the claims appended hereto.

The embodiment(s) described, and references in the specification to "one embodiment," "an embodiment," "an example embodiment," etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Before describing such embodiments in more detail, however, it is instructive to present an example environment in which embodiments of the present invention may be implemented.

Figure 1:
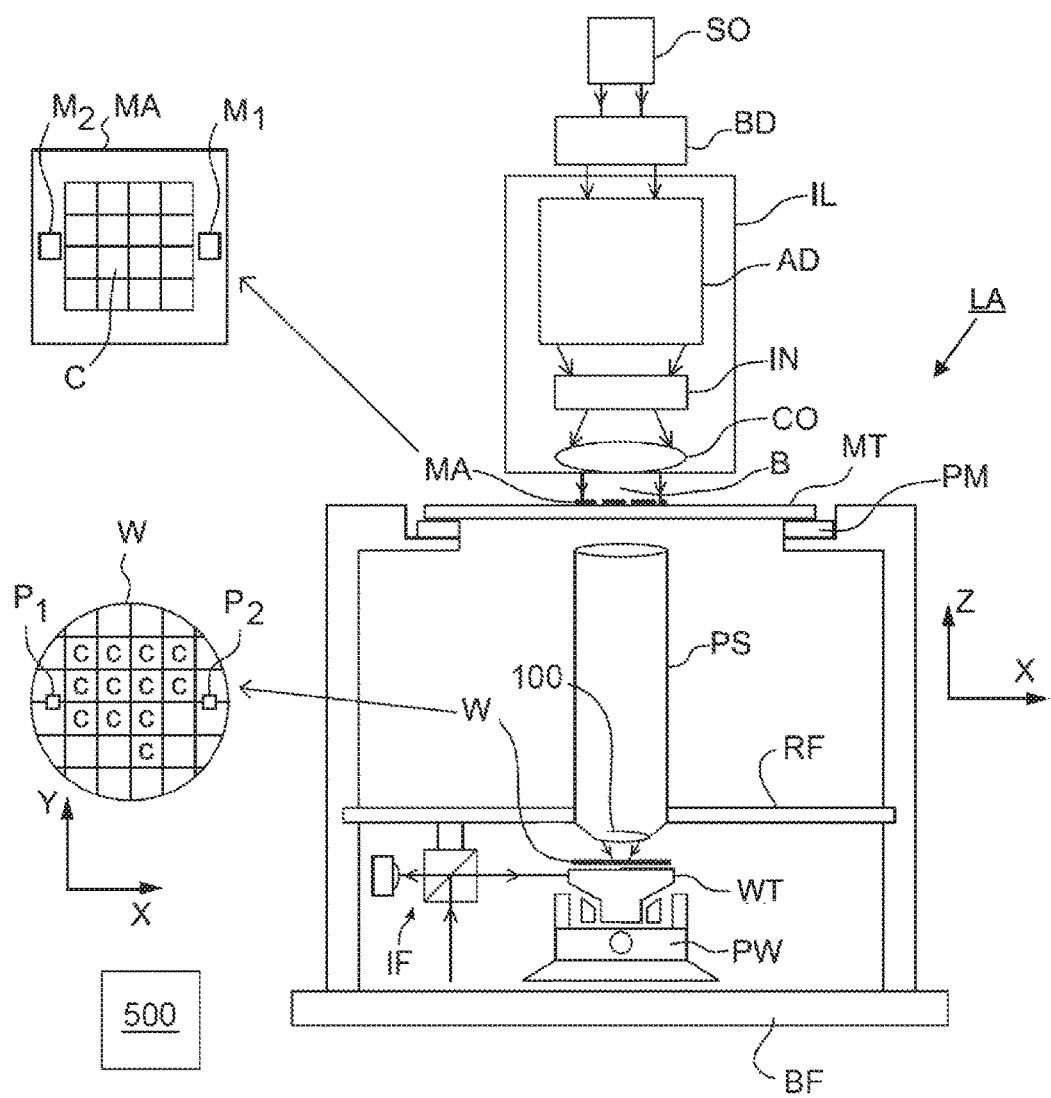
FIG. 1 depicts a lithographic apparatus.

FIG. 1 schematically depicts a lithographic apparatus LA. The apparatus includes an illumination system (illuminator) IL configured to condition a radiation beam B (e.g., UV radiation or DUV radiation), a support structure (e.g., a mask table) MT constructed to support a patterning device (e.g., a mask) MA and connected to a first positioner PM configured to accurately position the patterning device in accordance with certain parameters, a substrate table (e.g., a wafer table) WT constructed to hold a substrate (e.g., a resist coated wafer) W and connected to a second positioner PW configured to accurately position the substrate in accordance with certain parameters, and a projection system (e.g., a refractive projection lens system) PS configured to project a pattern imparted to the radiation beam B by patterning device MA onto a target portion C (e.g., comprising one or more dies) of the substrate W.

The illumination system may include various types of optical components, such as refractive, reflective, magnetic, electromagnetic, electrostatic, or other types of optical components, or any combination thereof, for directing, shaping, or controlling radiation.

The support structure supports, i.e., bears the weight of, the patterning device. It holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing various types of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system."

In this embodiment, for example, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may be of a type having two (dual stage) or more substrate tables and, for example, two or more mask tables. In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD for adjusting the angular intensity distribution of the radiation beam. Generally, at least the outer and/or inner radial extent (which are commonly referred to as σ-outer and σ-inner, respectively) of the intensity distribution in a pupil plane of the illuminator can be adjusted. In addition, the illuminator IL may comprise various other components, such as an integrator IN and a condenser CO. The illuminator may be used to condition the radiation beam to have a desired uniformity and intensity distribution in its cross section.

The radiation beam B is incident on the patterning device (e.g., mask MA), which is held on the support structure (e.g., mask table MT), and is patterned by the patterning device. Having traversed the mask MA, the radiation beam B passes through the projection system PS, which focuses the beam onto a target portion C of the substrate W. With the aid of the second positioner PW and position sensor IF (e.g., an interferometric device, linear encoder, 2-D encoder or capacitive sensor), the substrate table WT can be moved accurately, e.g., so as to position different target portions C in the path of the radiation beam B. Similarly, the first positioner PM and another position sensor (which is not explicitly depicted in FIG. 1) can be used to accurately position the mask MA with respect to the path of the radiation beam B, e.g., after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:

1. In step mode, the mask table MT and the substrate table WT are kept essentially stationary, while an entire pattern imparted to the radiation beam is projected onto a target portion C at one time (i.e., a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the mask table MT and the substrate table WT are scanned synchronously while a pattern imparted to the radiation beam is projected onto a target portion C (i.e., a single dynamic exposure). The velocity and direction of the substrate table WT relative to the mask table MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion.

3. In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
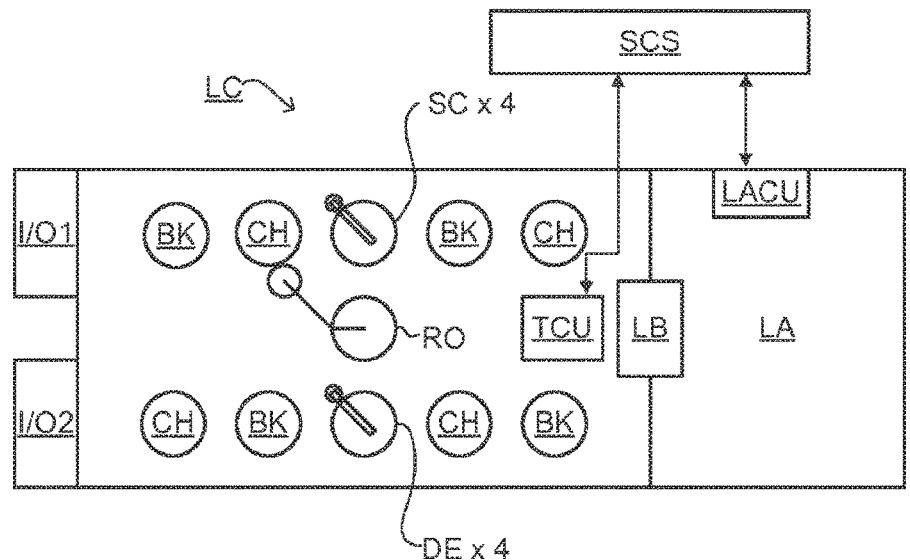
FIG. 2 depicts a lithographic cell or cluster.

As shown in FIG. 2 the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU that is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. If errors are detected, adjustments, for example, can be made to exposures of subsequent substrates, especially if the inspection can be done soon and fast enough that other substrates of the same batch are still to be exposed. Also, already exposed substrates may be stripped and reworked to improve yield, or possibly be discarded, thereby avoiding performing exposures on substrates that are known to be faulty. In a case where only some target portions of a substrate are faulty, further exposures can be performed only on those target portions that are deemed to be non-faulty.

An inspection apparatus is used to determine the properties of the substrates, and in particular, how the properties of different substrates or different layers of the same substrate vary from layer to layer. The inspection apparatus may be integrated into the lithographic apparatus LA or the lithocell LC or may be a stand-alone device. To enable most rapid measurements, it is desirable that the inspection apparatus measure properties in the exposed resist layer immediately after the exposure. However, the latent image in the resist has a very low contrast, as in there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB) that is customarily the first step carried out on exposed substrates and increases the contrast between exposed and unexposed parts of the resist. At this stage, the image in the resist may be referred to as semi-latent. It is also possible to make measurements of the developed resist image, at which point either the exposed or unexposed parts of the resist have been removed, or after a pattern transfer step such as etching. The latter possibility limits the possibilities for rework of faulty substrates but may still provide useful information.

Figure 3:
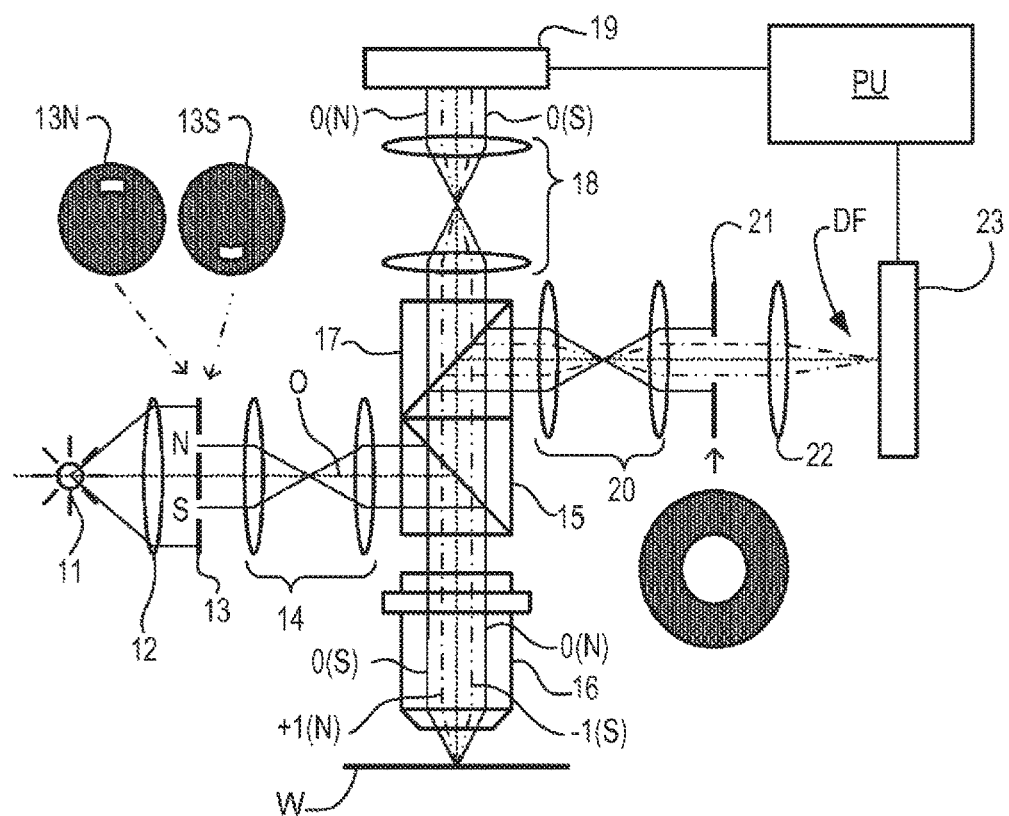
FIG. 3 depicts a scatterometer used in metrology.

FIG. 3 is a schematic diagram of an optical apparatus in the form of a scatterometer suitable for performing metrology in conjunction with the lithocell of FIG. 2. The apparatus may be used for measuring critical dimensions of features formed by lithography, measuring overlay between layers and the like. A product feature or dedicated metrology target is formed on substrate W. The apparatus may be a stand-alone device or incorporated in either the lithographic apparatus LA, e.g., at the measurement station, or the lithographic cell LC. An optical axis, which has several branches throughout the apparatus, is represented by a dotted line O. In this apparatus, light emitted by source 11 is directed onto substrate W via a beam splitter 15 by an optical system comprising lenses 12, 14 and objective lens 16. These lenses are arranged in a double sequence of a 4F arrangement. A different lens arrangement can be used, provided that it still provides an image of the source on the substrate, and simultaneously allows for access of an intermediate pupil-plane for spatial-frequency filtering. Therefore, the angular range at which the radiation is incident on the substrate can be selected by defining a spatial intensity distribution in a plane that presents the spatial spectrum of the substrate plane, here referred to as a (conjugate) pupil plane. In particular, this can be done by inserting an aperture plate 13 of suitable form between lenses 12 and 14, in a plane which is a back-projected image of the objective lens pupil plane. For example, as illustrated, aperture plate 13 can take different forms, two of which are labeled 13N and 13S, allowing different illumination modes to be selected. The illumination system in the illustrated example forms an off-axis illumination mode. In the first illumination mode, aperture plate 13N provides off-axis from a direction designated, for the sake of description only, as 'north'. In a second illumination mode, aperture plate 13S is used to provide similar illumination, but from an opposite direction, labeled 'south'. Other modes of illumination are possible by using different apertures. The rest of the pupil plane is desirably dark as any unnecessary light outside the desired illumination mode will interfere with the desired measurement signals.

At least the 0th and one of the −1 and +1 orders diffracted by the target on substrate W are collected by objective lens 16 and directed back through beam splitter 15. A second beam splitter 17 divides the diffracted beams into two measurement branches. In a first measurement branch, optical system 18 forms a diffraction spectrum (pupil plane image) of the target on first sensor 19 (e.g., a CCD or CMOS sensor) using the zeroth and first order diffractive beams. Each diffraction order hits a different point on the sensor, so that image processing can compare and contrast orders. The pupil plane image captured by sensor 19 can be used for focusing the metrology apparatus and/or normalizing intensity measurements of the first order beam. The pupil plane image can be used for many measurement purposes such as reconstruction.

In the second measurement branch, optical system 20, 22 forms an image of the target on the substrate W on sensor 23 (e.g., a CCD or CMOS sensor). In the second measurement branch, an aperture stop 21 is provided in a plane that is conjugate to the pupil-plane. Aperture stop 21 functions to block the zeroth order diffracted beam so that the image of the target formed on sensor 23 is formed only from the −1 or +1 first order beam. The image detected by sensor 23 is thus referred to as a 'dark-field' image. Note that the term 'image' is used here in a broad sense. An image of the grating lines as such will not be formed, if only one of the −1 and +1 orders is present.

The images captured by sensors 19 and 23 are output to image processor and controller PU, the function of which will depend on the particular type of measurements being performed.

Examples of scatterometers and techniques can be found in patent applications US 2006/066855 A1, WO 2009/078708, WO 2009/106279, and US 2011/0027704 A, which are all incorporated by reference herein in their entireties.

Figure 4:
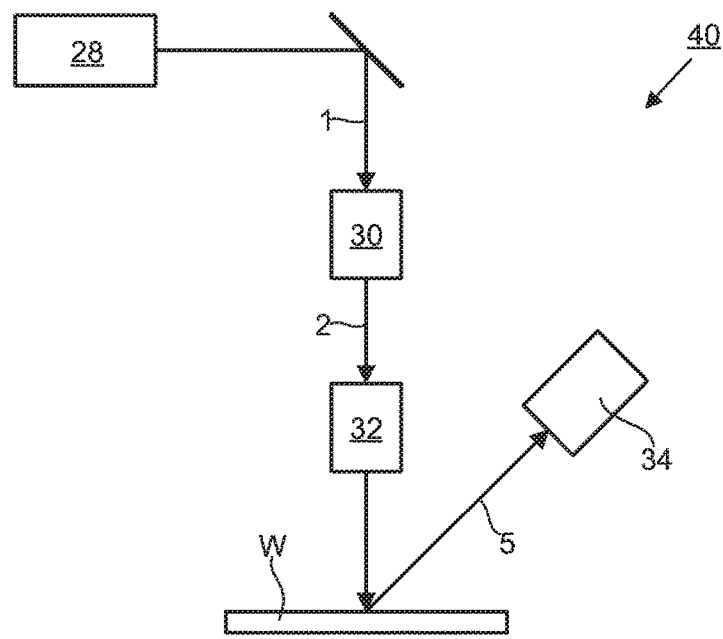
FIG. 4 depicts an inspection apparatus.

FIG. 4 depicts an inspection apparatus 40 according to an embodiment. The inspection apparatus 40 uses a radiation beam 1 with coherence, particularly high spatial coherence, such as a laser beam, provided by a source 28 (e.g. a laser). The radiation beam 1 is processed by a device 30 for processing a radiation beam with coherence. The device 30 outputs a processed radiation beam 2. The processed radiation beam 2 enters illumination optics 32. The illumination optics 32 direct the processed radiation beam 2 onto a target. In the example shown the target is provided on a substrate W. The illumination optics 32 may comprise elements corresponding to one or more of the elements in the optical path between source 11 and the substrate W in the arrangement of FIG. 3 for example (e.g. one or more of lenses 12, 14 and objective lens 16). The processed radiation beam 2 interacts with the target. A detector 34 detects radiation 5 originating from the processed radiation beam 2 after interaction of the processed radiation beam 2 with the target. The detector 34 may comprise one or more measurement branches as described above with reference to FIG. 3 for example. An output from the detector 34 is used to determine properties such as overlay errors between subsequent layers, line thicknesses, critical dimensions (CD), etc., of the substrate W (e.g. using an image processor and controller PU as described above with reference to FIG. 3).

Radiation beams with high spatial coherence, such as laser beams, can provide high brightness but can also be susceptible to variations in spatial uniformity and/or instabilities in time. Variations in spatial uniformity can occur due to interference effects arising as a result of the high spatial coherence in the radiation beam. The phenomenon known as speckle is a well known interference effect associated with laser beams. Instability in time can occur due to fluctuations in the distribution of radiation between different radiation beam spatial modes. Fluctuation in the distribution of radiation between different radiation beam spatial modes can cause a spatial intensity distribution over a target to fluctuate in time (even if the total intensity remains constant in time). Pointing instability is a known phenomenon arising from such fluctuation.

In a radiation beam with high spatial coherence, the radiation beam comprises components which are distributed over a relatively small number of radiation beam spatial modes. The distribution will depend on details of the source that provides the radiation beam. In the case of a laser, for example, the distribution between the radiation beam spatial modes may be determined by the size and/or geometry of the optical resonator and/or associated aperture of the laser. The radiation beam spatial modes may comprise one or more transverse spatial modes. In the case of a radiation beam having cylindrical symmetry, the transverse spatial mode patterns may be described by a combination of a Gaussian beam profile with a Laguerre polynomial. Such modes are denoted $TEM_{pl}$ where p and l are integers labeling the radial and angular mode orders respectively. Note that when spatial modes are mentioned these may also be understood to be expressed in another basis, for example a basis of plane waves or a basis of diffraction limited spots or a basis of speckle patterns.

A radiation beam with coherence, particularly high spatial coherence, may comprise at least one radiation beam spatial mode comprising a plurality of components. The radiation beam spatial mode is thus common to all of the plurality of components that are in that radiation beam spatial mode. The radiation beam spatial mode may be referred to as the common radiation beam spatial mode with respect to the plurality of components. Each of the plurality of components in the common radiation beam spatial mode has a different wavelength or range of wavelengths. The plurality of components may together provide a continuous range of wavelengths within the common radiation beam spatial mode. Alternatively or additionally, the plurality of components may provide two or more wavelengths or ranges of wavelengths which are separated from each other by a range of wavelengths which are not present in the common radiation beam spatial mode.

Figures 5, 6, 7:
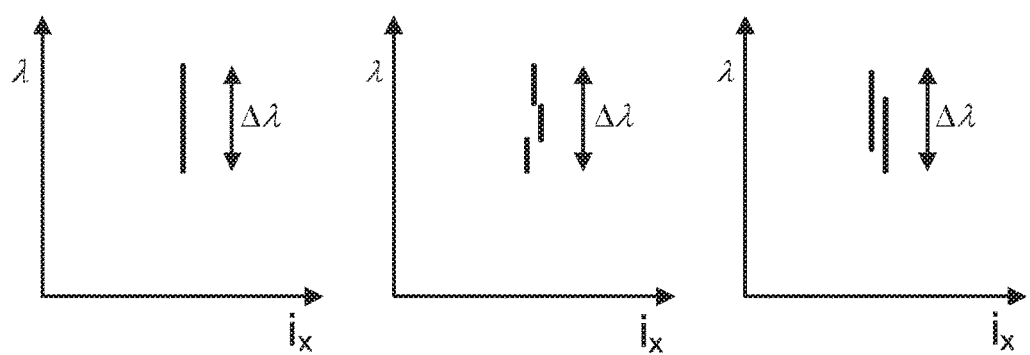
FIGS. 5-7 depict example compositions of a radiation beam to be processed.

FIGS. 5-7 depict the composition of three example radiation beams with high spatial coherence. Wavelength λ of the radiation beam is depicted on the vertical axis. An index representing the spatial mode $i_x$ is depicted on the horizontal axis. Each different value of the index $i_x$ represents a different radiation beam spatial mode. In the example of FIG. 5, all components of the radiation beam are in the same radiation beam spatial mode. A plurality of components provide a continuous range of wavelengths spread over a spectral bandwidth Δλ. In the example of FIG. 6, the radiation beam comprises components distributed over three radiation beam spatial modes. In this example, each of the three radiation beam spatial modes comprises a plurality of components having different wavelengths. There is no overlap in wavelength between components in different radiation beam spatial modes. Taken together, the components of the radiation beam are spread over a spectral bandwidth Δλ. In the example of FIG. 7, the radiation beam comprises components distributed over two radiation beam spatial modes. Both of the radiation beam spatial modes comprise a plurality of components having different wavelengths. In this example, there is overlap in wavelength between components in different radiation beam spatial modes. Taken together, the components of the radiation beam are spread over a spectral bandwidth Δλ. A radiation beam may fluctuate in time. For example, the composition of the radiation beam may randomly alternate between the compositions depicted in FIGS. 5-7.

Figure 8:
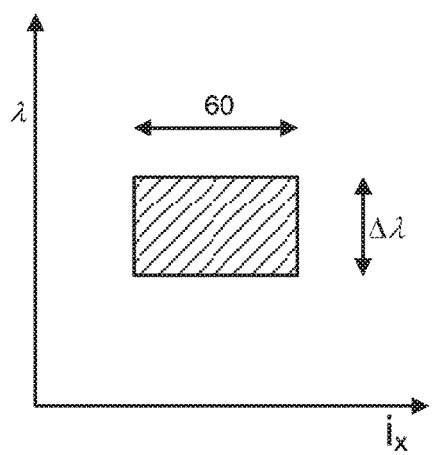
FIG. 8 depicts a composition of processed radiation beam.

In an embodiment, the device 30 is configured to process the radiation beam 1 in such a way as to increase the range of spatial modes over which the components of the radiation beam 1 are spread. This is achieved without requiring any moving components. All components of the device 30 are static with respect to each other. The device 30 takes as input a radiation beam 1 having a spectral bandwidth Δλ with components in an arbitrary (and potentially unknown) distribution over a relatively small number of radiation beam spatial modes. The device 30 outputs a processed radiation beam 2 having components distributed over a wider range of radiation beam spatial modes. The composition of an example processed radiation beam 2 is depicted in FIG. 8. The input radiation beam 1 may have the form of any of the radiation beams represented by FIGS. 5-7 for example. The spectral bandwidth Δλ of the processed radiation beam 2 is the same as the spectral bandwidth of the input radiation beam 1. However, the wider range of radiation beam spatial modes, to which light is coupled incoherently, provides a larger étendue 60 in the processed radiation beam 2 than in the input radiation beam 1. The larger étendue 60 reduces interference effects, thereby providing high uniformity. Radiation in different radiation beam spatial modes combines incoherently at the target. Instabilities over time caused by fluctuations in the distribution of the light between different radiation beam spatial modes are averaged over a higher number of radiation beam spatial modes, thereby reducing the overall size of any resulting intensity fluctuations. Stability over time is thereby improved.

In an embodiment, the range of radiation beam spatial modes in the processed radiation beam 2 is controlled to be large enough substantially to eliminate interference effects such as speckle but small enough to avoid excess loss of light due to aperture stops in the illumination optics 32 or overfilling of the target. In an embodiment, the range of radiation beam spatial modes is selected to provide an étendue 60 which at least substantially matches an étendue of the illumination optics 32 and the target on the substrate W (so as not to lose to much of the radiation beam).

Figure 9:
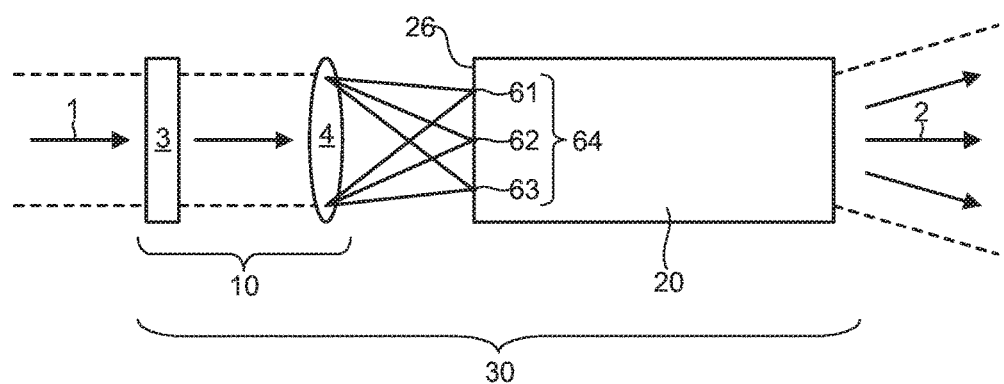
FIG. 9 depicts a device for processing a radiation beam with coherence.
Figure 10:
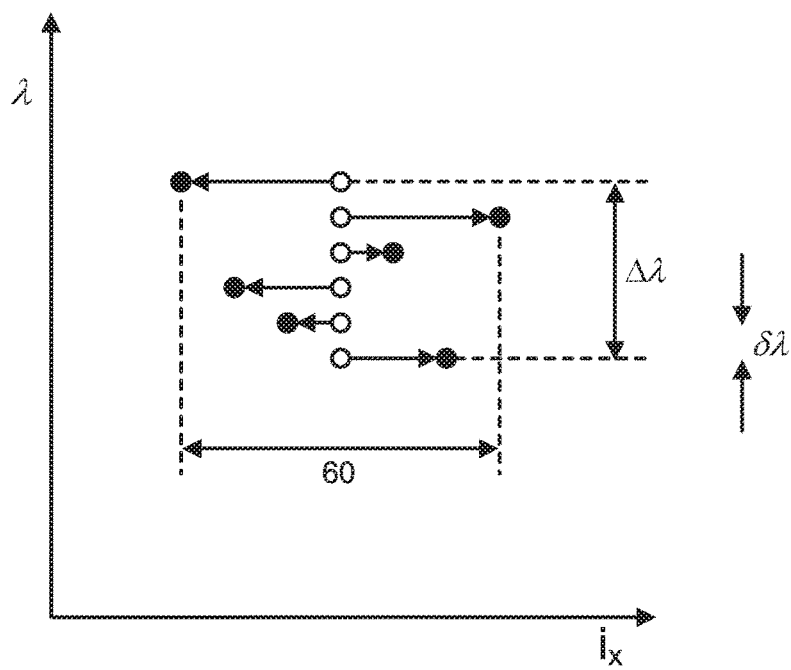
FIG. 10 depicts distribution of components of a radiation beam over different waveguide spatial modes.

FIG. 9 depicts an example configuration for the device 30. In this embodiment, the device 30 comprises an optical system 10 and a waveguide 20. The optical system 10 receives a radiation beam 1 with coherence (e.g. a radiation beam with high spatial coherence such as a laser beam). The radiation beam 1 comprises components distributed over one or more radiation beam spatial modes. The radiation beam 1 comprises a plurality of components in at least one of the radiation beam spatial modes. For these plurality of components the radiation beam spatial mode is referred to as a common radiation beam spatial mode. FIG. 10 depicts the composition of an example common radiation beam spatial mode. In this example the common radiation beam spatial mode comprises six components (depicted by open circles). Each of the six components has a different wavelength or range of wavelengths. As discussed above, the six components may constitute a continuous range of wavelengths or may be separated from each other. The six components have a spectral bandwidth of Δλ and are separated from each other by δλ.

The waveguide 20 supports a plurality of waveguide spatial modes (i.e. a plurality of waveguide spatial modes are available for radiation propagating within the waveguide). The waveguide 20 is a structure that guides radiation and may take any of the various forms known in the art. In an embodiment, the waveguide comprises or consists of an optical waveguide such as an optical fiber. In this case the waveguide spatial modes are provided by the modes of the optical fiber. The optical fiber may be a multi-mode optical fiber. The number of modes of the optical fiber may be determined in this case by the expression $V = k_0 a \sqrt{n_1^2 - n_2^2}$ where $k_0$ is the wave number, a is the fiber's core radius, and $n_1$ and $n_2$ are the refractive indices of the core and cladding respectively. For a step-index fiber with large V the number of modes is approximately proportional to $V^2$. In other embodiments, the waveguide 20 comprises or consists of one or more of the following in any combination: a mixing tube, a mixing rod, a graded index fiber, and a light pipe.

The optical system 10 and the waveguide 20 interact to distribute the components that are initially in the common radiation beam spatial mode between a plurality of different waveguide spatial modes (depicted by filled circles in FIG. 10), thereby increasing the étendue 60 of the radiation beam and reducing interference effects and instabilities over time. This is achieved by configuring the optical system 10 to direct a plurality of the components of the radiation beam belonging to a common radiation beam spatial mode and having different frequencies (e.g. the open circles in FIG. 10) onto the waveguide 20 in such a way that each of the plurality of components couples to a different set of the waveguide spatial modes (i.e. different to the set to which any of the other components of the plurality of components couples). Each set comprises one or more of the waveguide spatial modes. Two or more of the different sets may overlap with each other (i.e. have one or more waveguide spatial modes in common) or may be mutually exclusive (i.e. have no waveguide spatial modes in common). Thus, the different spectral properties of components having the same spatial characteristics in the input radiation beam are used to distribute the components between different waveguide spatial modes, thereby providing a spread in the spatial characteristics of the radiation and increased étendue 60.

In an embodiment, of which FIG. 9 is an example, the optical system 10 is configured such that each of the plurality of components belonging to the common radiation beam spatial mode and having different frequencies enters the waveguide 20 at a different position, in a different direction, or both, thereby achieving the coupling to the different sets of waveguide spatial modes. In the example of FIG. 9, the input radiation beam 1 is focused onto a plurality of regions 61-63 (referred to collectively as regions 64). Each of the regions 64 respectively receives radiation from a different one of a plurality of components belonging to a common radiation beam spatial mode and having different frequencies. The radiation enters the waveguide 20 at a different position and in a different direction at each of the different regions 64.

In an embodiment, of which FIG. 9 is also an example, the waveguide 20 comprises an input interface 26 that receives the radiation beam from the optical system 10. In an embodiment the input interface 26 comprises an interface between a solid material through which radiation will propagate inside the waveguide 20 and a gaseous material such as air located outside of the waveguide 20. The optical system 10 directs each of the plurality of components belonging to the common radiation beam spatial mode and having different frequencies onto a different position 64 on the input interface 26, thereby achieving the coupling to the different sets of the waveguide spatial modes. In an embodiment the input interface 26 is a smooth surface, for example a planar surface. In other embodiments, the input interface 26 is provided with surface roughness and/or is otherwise non-planar. Providing an input interface 26 that has surface roughness and/or which is otherwise non-planar may increase the randomness (or uniformity) of coupling to the different sets of waveguide spatial modes. Increasing the randomness (or uniformity) of the coupling may further improve the spatial uniformity of intensity of the processed radiation beam 2 at the target.

The optical system 10 redirects radiation differently as a function of the wavelength of the radiation in order to achieve the coupling to the different sets of waveguide spatial modes. This functionality may be provided in a variety of different ways. In the particular example of FIG. 9, a diffraction grating 3 is used to provide the wavelength dependence. The diffraction grating 3 is depicted as a transmissive grating but a reflective grating could be used instead. A lens 4 is provided to at least partially focus radiation onto the waveguide 20. The lens 4 is not essential. The lens 4 could be a cylindrical lens. In other embodiments, a prism or a diffuser or a 2D diffraction grating is used in place of the diffraction grating 3 or in combination with a diffraction grating.

In an embodiment, the waveguide 20 is configured to support at least two different waveguide spatial modes in respect of light in the visible spectrum. Typically, however, it will be desirable to use a waveguide 20 that can support many more waveguide spatial modes, for example more than 100 waveguide spatial modes in respect of light in the visible spectrum, optionally more than 1000 waveguide spatial modes in respect of light in the visible spectrum, optionally more than $10^4$ waveguide spatial modes in respect of light in the visible spectrum, optionally more than $10^5$ waveguide spatial modes in respect of light in the visible spectrum. Using a waveguide 20 that supports a large number of waveguide spatial modes can increase the randomness (or uniformity) of coupling to the different sets of waveguide spatial modes. Increasing the randomness (or uniformity) of the coupling may improve the spatial uniformity of intensity of the processed radiation beam 2 at the target.

As mentioned above it is also desirable to provide an étendue which is not too large. This may be achieved by ensuring that the waveguide 20 does not support more spatial modes that the rest of the system, including illumination optics, target and detector. This typically means the waveguide should support less than about $10^8$ waveguide spatial modes in respect of light in the visible spectrum.

The number of waveguide spatial modes has been defined above in respect of light in the visible spectrum for the purposes of clarity, because the number of waveguide spatial modes depends on the wavelength of the radiation that is propagating within the waveguide 20. It will be understood that the device 30 need not necessarily be used exclusively with visible light. The device 30 may be used with radiation having one or more components with wavelengths longer than any visible light, wavelengths within the visible spectrum, or wavelengths shorter than any visible light.

In an embodiment the cross-section of the waveguide 20 is circular, as in a standard optical fiber for example. Waveguides of this type are easy to obtain and/or manufacture.

Figure 11:
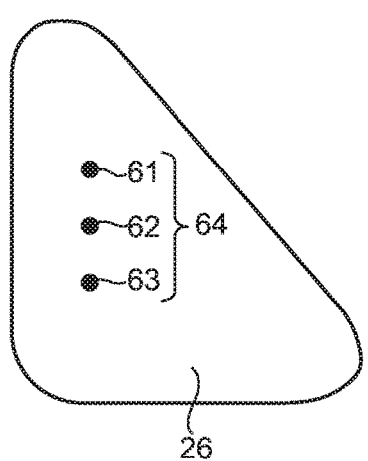
FIG. 11 depicts an asymmetric waveguide cross-section.
Figure 13:
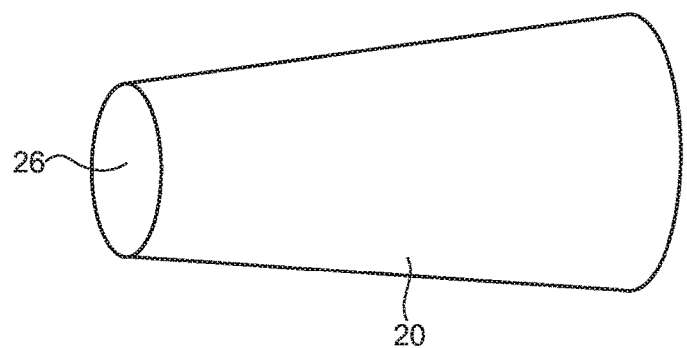
FIG. 13 depicts a waveguide having a cross-section which varies along a longitudinal axis of the waveguide.

In an alternative embodiment, the cross-section of the waveguide 20 (perpendicular to a longitudinal axis of the waveguide) is non-circular. An example of such a cross-section is depicted in FIG. 11. Reducing the symmetry of the waveguide 20 may change the shape of the waveguide modes, for example from Laguerre-Gaussian towards speckle patterns. This may increase the randomness (or uniformity) of coupling to the different sets of waveguide spatial modes. Increasing the randomness (or uniformity) of the coupling may improve the spatial uniformity of intensity of the processed radiation beam 2 at the target. The symmetry may be reduced in various different ways. In an embodiment, the cross-section of the waveguide 20 is shaped so as to have no rotational symmetry, no mirror symmetry, or no rotational symmetry and no mirror symmetry. In an embodiment, the cross-section has the shape of a mathematically chaotic, theoretical billiard table (i.e. a billiard table shaped such that the dynamical properties of billiard balls moving within the confines of the table are mathematically chaotic). In other embodiments, the symmetry of the waveguide 20 is reduced additionally or alternatively by providing a waveguide 20 in which a cross-section of the waveguide 20 varies as a function of position along a longitudinal axis of the waveguide 20. An example of such an embodiment is shown in FIG. 13.

Alternatively or additionally, in an embodiment a symmetry of the waveguide 20 is reduced by configuring the waveguide 20 such that radiation propagating in the waveguide 20 propagates through a material having a refractive index that varies as a function of position in the waveguide 20. In embodiments of this type, the variation in refractive index will provide an increase in the randomness of coupling to waveguide spatial modes even in the case where the waveguide 20 is otherwise highly symmetric (e.g. an optical fiber with a cross-section that is constant along the longitudinal axis and/or circular).

Figure 12:
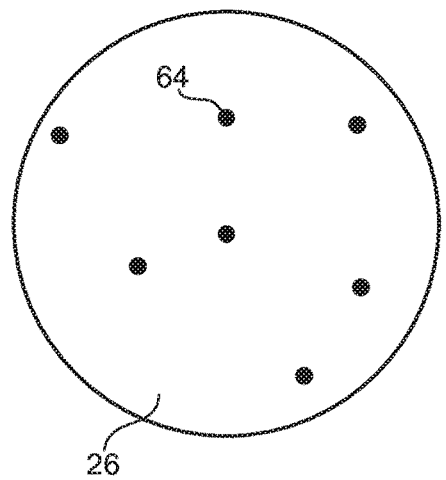
FIG. 12 depicts an asymmetric distribution of components of a radiation beam onto an interface surface of a symmetric waveguide.

In an embodiment, the optical system 10 is configured to direct the plurality of components of the radiation beam onto the waveguide 20 in a non-symmetric manner to increase the randomness of coupling to waveguide spatial modes. This may be particularly beneficial where the waveguide 20 itself has relatively high symmetry (e.g. an optical fiber with a cross-section that is constant along the longitudinal axis and/or circular). An example distribution of regions 64 of input radiation from such an optical system 10 on an input interface 26 is depicted in FIG. 12. It is desirable to cover the input interface 26 of the waveguide 20 as uniformly as possible, optionally up to the case where the number of regions 64 is arranged to be substantially equal to the number of waveguide spatial modes and/or the regions 64 fully cover the input interface 26 and/or couple to all available waveguide spatial modes. Thus, in an embodiment the optical system 10 and waveguide 20 are configured such that substantially all (e.g. at least 90%, optionally at least 95%, optionally at least 99%) of the waveguide spatial modes supported by the waveguide 20 are substantially uniformly (and incoherently) populated.

Figure 14:
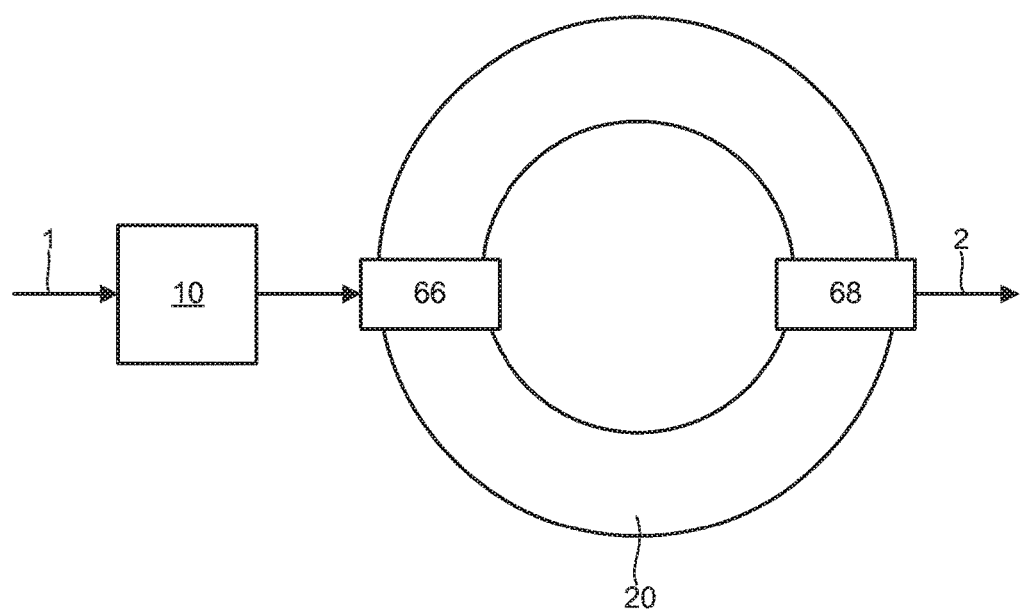
FIG. 14 depicts a waveguide forming a closed loop.

In an embodiment, the waveguide 20 is configured to allow one or more of the plurality of components of the radiation beam directed onto the waveguide 20 to propagate backwards and forwards through the waveguide 20 a plurality of times (e.g. by repeated reflection from interfaces provided at extreme ends of the waveguide 20. Alternatively, as shown schematically in FIG. 14, the waveguide 20 may form a closed loop, for example by being formed in a toroidal or donut shape. The waveguide 20 in such an embodiment is configured so that one or more of the plurality of components of the radiation beam directed onto the waveguide 20 propagate a plurality of times around the closed loop. Radiation may enter the waveguide 20 at input 66 (e.g. using a suitably angled partially reflective interface) and leave the waveguide 20 at output 66 (e.g. using a further suitably angled partially reflective interface), optionally after having propagated around the closed loop on average a plurality of times. Increasing the average distance of travel through the waveguide 20 may further improve the spatial uniformity of intensity of the processed radiation beam 2 at the target.

The above embodiments and other embodiments may be used in a method of processing a radiation beam with coherence. The method comprises receiving a radiation beam 1 with coherence. The radiation beam 1 comprises components distributed over one or more radiation beam spatial modes. The method further comprises passing the radiation beam 1 through an optical system 10. The optical system 10 directs the components onto a waveguide 20 supporting a plurality of waveguide spatial modes. The optical system 10 directs a plurality of the components of the radiation beam belonging to a common radiation beam spatial mode and having different frequencies onto the waveguide 20 in such a way that each of the plurality of components couple to a different set of the waveguide spatial modes, each set comprising one or more of the waveguide spatial modes.

The above embodiments and other embodiments may be used in a method of inspecting a target. The method comprises processing a radiation beam 1 using a device 30 of an embodiment. The method further comprises directing the processed radiation beam 2 onto the target. The method further comprises detecting radiation originating from the processed radiation beam 2 after interaction of the processed radiation beam 2 with the target.

The above embodiments and other embodiments may be used in a method of performing a lithographic process. The method comprises the steps of forming device structures and at least one metrology target on a substrate by the lithographic process. The method further comprises inspecting the metrology target using the method of processing a radiation beam of an embodiment. The method further comprises controlling subsequent processing of the substrate and/or further substrates in accordance with a measured value obtained by the inspecting of the metrology target.

The above embodiments and other embodiments may be used in a lithographic apparatus, for example a lithographic apparatus as described above with reference to FIG. 1. The lithographic apparatus comprises the device 30. A processed radiation beam produced by the device is directed to a patterning device MA. The patterning device MA is configured to impart the processed radiation beam with a pattern in its cross-section to form a patterned radiation beam. A projection system PS projects the patterned radiation beam onto a substrate.

The above embodiments and other embodiments may be used in a method of performing a lithographic process. The method comprises the method of processing a radiation beam of an embodiment. The processed radiation beam is directed onto a patterning device MA to produce a patterned radiation beam. The patterned radiation beam is projected onto a substrate W.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

Further embodiments according to the invention are described in below numbered clauses:

1. A device for processing a radiation beam with coherence, comprising:

an optical system configured to receive a radiation beam with coherence, the radiation beam comprising components distributed over one or more radiation beam spatial modes; and a waveguide configured to support a plurality of waveguide spatial modes, wherein:

the optical system is configured to direct a plurality of the components of the radiation beam belonging to a common radiation beam spatial mode and having different frequencies onto the waveguide in such a way that each of the plurality of components couples to a different set of the waveguide spatial modes, each set comprising one or more of the waveguide spatial modes.

2. The device of clause 1, wherein the optical system is configured such that each of the plurality of components belonging to the common radiation beam spatial mode and having different frequencies enters the waveguide at a different position, in a different direction, or both, thereby achieving the coupling to the different sets of waveguide spatial modes.

3. The device of clause 2, wherein the coupling to the different sets of waveguide spatial modes is such that substantially all of the waveguide spatial modes supported by the waveguide are substantially uniformly populated.

4. The device of clause 2 or 3, wherein the waveguide comprises an input interface through which radiation can enter the waveguide, and the optical system is configured to direct each of the plurality of components belonging to the common radiation beam spatial mode and having different frequencies onto a different position on the input interface, thereby achieving the coupling to the different sets of the waveguide spatial modes.

5. The device of clause 4, wherein the input interface is non-planar.

6. The device of any preceding clause, wherein the waveguide supports more than 100 waveguide spatial modes in respect of light in the visible spectrum.

7. The device of any preceding clause, wherein the waveguide supports less than $10^8$ waveguide spatial modes in respect of light in the visible spectrum.

8. The device of any preceding clause, wherein a cross-section of the waveguide is circular.

9. The device of any of clauses 1-7, wherein a cross-section of the waveguide is non-circular.

10. The device of clause 9, wherein the cross-section of the waveguide has no rotational symmetry, no mirror symmetry, or no rotational symmetry and no mirror symmetry.

11. The device of any preceding clause, wherein the waveguide is configured to allow one or more of the plurality of components of the radiation beam directed onto the waveguide to propagate backwards and forwards through the waveguide a plurality of times.

12. The device of any of clause 1-10, wherein the waveguide forms a closed loop and is configured so that one or more of the plurality of components of the radiation beam directed onto the waveguide propagate a plurality of times around the closed loop.

13. The device of any preceding clause, wherein a cross-section of the waveguide varies as a function of position along a longitudinal axis of the waveguide.

14. The device of any preceding clause, configured such that a material through which radiation propagates in the waveguide in use has a refractive index that varies as a function of position in the waveguide.

15. The device of any preceding clause, wherein the optical system comprises one or more of the following in any combination: a diffraction grating, a prism, a diffuser.

16. The device of any preceding clause, wherein the waveguide comprises one or more of the following: an optical fibre, a graded index optical fiber, a mixing tube, a mixing rod, and a light pipe.

17. The device of any preceding clause, wherein the radiation beam with coherence comprises a laser beam.

18. An inspection apparatus for inspecting a target, comprising:

the device for processing a radiation beam with coherence of any preceding clause;

illumination optics for directing a processed radiation beam produced by the device onto the target; and a detector for detecting radiation originating from the processed radiation beam after interaction of the processed radiation beam with the target.

19. A lithographic apparatus, comprising:

the device for processing a radiation beam with coherence of any of clauses 1-17 to produce a processed radiation beam;

a patterning device configured to impart the processed radiation beam with a pattern in its cross-section to form a patterned radiation beam; and a projection system configured to project the patterned radiation beam onto a substrate.

20. A method of processing a radiation beam with coherence, comprising:

receiving a radiation beam with coherence, the radiation beam comprising components distributed over one or more radiation beam spatial modes;

passing the radiation beam through an optical system which directs the components onto a waveguide supporting a plurality of waveguide spatial modes, wherein:

the optical system directs a plurality of the components of the radiation beam belonging to a common radiation beam spatial mode and having different frequencies onto the waveguide in such a way that each of the plurality of components couples to a different set of the waveguide spatial modes, each set comprising one or more of the waveguide spatial modes.

21. A method of inspecting a target, comprising:

processing a radiation beam using the method of clause 20;

directing the processed radiation beam onto the target; and detecting radiation originating from the processed radiation beam after interaction of the processed radiation beam with the target.

22. A method of performing a lithographic process, comprising:

forming device structures and at least one metrology target on a substrate by said lithographic process;

inspecting the metrology target using the method of clause 21; and controlling subsequent processing of the substrate and/or further substrates in accordance with a measured value obtained by the inspecting of the metrology target.

23. A method of performing a lithographic process, comprising:

processing a radiation beam using the method of clause 20;

directing the processed radiation beam onto a patterning device to produce a patterned radiation beam; and projecting the patterned radiation beam onto a substrate.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens," where the context allows, may refer to any one or combination of various types of optical components, including refractive, reflective, magnetic, electromagnetic, and electrostatic optical components.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:

1. A device for processing a radiation beam with coherence, comprising:
    an optical system configured to receive a radiation beam with coherence, the radiation beam comprising components distributed over one or more radiation beam spatial modes; and
    a waveguide configured to support a plurality of waveguide spatial modes,
    wherein the optical system is configured to direct a plurality of the components of the radiation beam belonging to a common radiation beam spatial mode and having different frequencies onto the waveguide in such a way that each of the plurality of components couples to a different set of the waveguide spatial modes, each set comprising one or more of the waveguide spatial modes.

2. The device of claim 1, wherein the optical system is configured such that each of the plurality of components belonging to the common radiation beam spatial mode and having different frequencies enters the waveguide at a different position, in a different direction, or both, thereby achieving the coupling to the different sets of waveguide spatial modes.

3. The device of claim 2, wherein the coupling to the different sets of waveguide spatial modes is such that substantially all of the waveguide spatial modes supported by the waveguide are substantially uniformly populated.

4. The device of claim 2, wherein the waveguide comprises:
    an input interface through which radiation can enter the waveguide, and
    the optical system is configured to direct each of the plurality of components belonging to the common radiation beam spatial mode and having different frequencies onto a different position on the input interface, thereby achieving the coupling to the different sets of the waveguide spatial modes.

5. The device of claim 4, wherein the input interface is non-planar.

6. The device of claim 1, wherein the waveguide supports more than 100 waveguide spatial modes in respect of light in the visible spectrum.

7. The device of claim 1, wherein the waveguide supports less than $10^8$ waveguide spatial modes in respect of light in the visible spectrum.

8. The device of claim 1, wherein a cross-section of the waveguide is circular.

9. The device of claim 1, wherein a cross-section of the waveguide is non-circular.

10. The device of claim 9, wherein the cross-section of the waveguide has no rotational symmetry, no mirror symmetry, or no rotational symmetry and no mirror symmetry.

11. The device of claim 1, wherein the waveguide is configured to allow one or more of the plurality of components of the radiation beam directed onto the waveguide to propagate backwards and forwards through the waveguide a plurality of times.

12. The device of claim 1, wherein the waveguide forms a closed loop and is configured so that one or more of the plurality of components of the radiation beam directed onto the waveguide propagate a plurality of times around the closed loop.

13. The device of claim 1, wherein a cross-section of the waveguide varies as a function of position along a longitudinal axis of the waveguide.

14. The device of claim 1, configured such that a material through which radiation propagates in the waveguide in use has a refractive index that varies as a function of position in the waveguide.

15. The device of claim 1, wherein the optical system comprises one or more of the following in any combination:
    a diffraction grating,
    a prism, and
    a diffuser.

16. The device of claim 1, wherein the waveguide comprises one or more of the following:
    an optical fiber,
    a graded index optical fiber,
    a mixing tube,
    a mixing rod, and
    a light pipe.

17. The device of claim 1, wherein the radiation beam with coherence comprises a laser beam.

18. An inspection apparatus for inspecting a target, comprising:
    a device configured to process a radiation beam with coherence, comprising:
        an optical system configured to receive a radiation beam with coherence, the radiation beam comprising components distributed over one or more radiation beam spatial modes; and
        a waveguide configured to support a plurality of waveguide spatial modes,
        wherein the optical system is configured to direct a plurality of the components of the radiation beam belonging to a common radiation beam spatial mode and having different frequencies onto the waveguide in such a way that each of the plurality of components couples to a different set of the waveguide spatial modes, each set comprising one or more of the waveguide spatial modes;

illumination optics configured to direct a processed radiation beam produced by the device onto the target; and a detector configured to detect radiation originating from the processed radiation beam after interaction of the processed radiation beam with the target.

19. A lithographic apparatus, comprising:

a device configured to process a radiation beam with coherence to produce a processed radiation beam, the device comprising:

an optical system configured to receive a radiation beam with coherence, the radiation beam comprising components distributed over one or more radiation beam spatial modes; and a waveguide configured to support a plurality of waveguide spatial modes, wherein the optical system is configured to direct a plurality of the components of the radiation beam belonging to a common radiation beam spatial mode and having different frequencies onto the waveguide in such a way that each of the plurality of components couples to a different set of the waveguide spatial modes, each set comprising one or more of the waveguide spatial modes;

a patterning device configured to impart the processed radiation beam with a pattern in its cross-section to form a patterned radiation beam; and a projection system configured to project the patterned radiation beam onto a substrate.

* * * * *